United States Patent [19]

Yates et al.

[11] Patent Number: 5,336,377

[45] Date of Patent: Aug. 9, 1994

[54] PROCESS FOR REMOVING 2-CHLORO-1,1-DIFLUOROETHYLENE FROM 1,1,1,2-TETRAFLUOROETHANE AND CO-PRODUCING 2-CHLORO-1,1,1,2-TETRAFLUOROETHANE

[75] Inventors: Stephen F. Yates, Rolling Meadows, Ill.; Daniel F. Harnish, Orchard Park; Addison M. Smith, Amherst, both of N.Y.

[73] Assignee: Allied-Signal Inc., Morris Township, Morris County, N.J.

[21] Appl. No.: 809,808

[22] Filed: Dec. 18, 1991

[51] Int. Cl.$^5$ .................. B01D 3/34; C07C 17/00
[52] U.S. Cl. ................. 203/29; 203/DIG. 6; 203/DIG. 16; 204/59 F; 204/158.11; 570/177; 570/178
[58] Field of Search .............. 203/29, 91, DIG. 16, 203/DIG. 6; 570/177, 178, 134; 204/59 F, 158.11

[56] References Cited

U.S. PATENT DOCUMENTS

| 2,436,135 | 2/1948 | Barrick et al. | 204/158.11 |
| 3,046,304 | 7/1962 | Neville | 204/158.11 |
| 3,214,478 | 10/1965 | Millan, Jr. | 204/157.92 |
| 3,444,249 | 5/1969 | Regan | 204/158.11 |
| 3,554,887 | 1/1971 | Feehs | 204/158.11 |
| 3,686,082 | 8/1972 | Ruehlen | 204/158.11 |
| 3,819,483 | 6/1974 | Fozzard | 203/70 |
| 4,129,603 | 12/1978 | Bell | 260/653 |
| 4,158,675 | 6/1979 | Potter | 260/653.7 |
| 4,906,796 | 3/1990 | Yates | 570/179 |
| 4,948,479 | 8/1990 | Brooks et al. | 204/158.21 |

FOREIGN PATENT DOCUMENTS

| 0249265 | 1/1924 | Australia | 204/158.11 |
| 0743925 | 10/1966 | Canada | 204/158.11 |
| 0143864 | 6/1985 | European Pat. Off. . | |
| 0401493 | 12/1990 | European Pat. Off. . | |
| 0698127 | 10/1953 | United Kingdom . | |

OTHER PUBLICATIONS

Yano et al, J. Chem. Phys. vol. 72, No. 5, Mar. 1, 1980, "Vacuum–ultraviolet (147 nm) photodecomposition of 1,1,2–trichloro–2,2–difluoroethane."

Yano et al, The Journal of Physical Chemistry, vol. 83, No. 20, 1979, pp. 2572–2577 "Photodecomposition of 1,1–Difluoroethane at 147 nm."

Gordon A. J. and R. A. Ford, *The Chemists Companion*, Wiley Interscience (1972), pp. 362–368.

Primary Examiner—Virginia Manoharan
Attorney, Agent, or Firm—Harold N. Wells; Mary Jo Boldingh; Jay P. Friedenson

[57] ABSTRACT

2-Chloro-1,1-difluoroethylene (R-1122) is removed from 1,1,1,2-tetrafluoroethane (R-134a) by contacting the R-134a in the vapor phase with chlorine in the presence of ultraviolet light providing an exposure of at least about 2 watts-hour/kg.

8 Claims, 2 Drawing Sheets

PROCESS FOR REMOVING 2-CHLORO-1,1-DIFLUOROETHYLENE FROM 1,1,1,2-TETRAFLUOROETHANE AND CO-PRODUCING 2-CHLORO-1,1,1,2-TETRAFLUOROETHANE

BACKGROUND OF THE INVENTION

This invention relates principally to the purification of 1,1,1,2-tetrafluoroethane, also designated R-134a, which has been of particular interest as a replacement for chlorofluorocarbons having similar physical properties, particularly R-12. R-134a may be prepared by reaction of other fluorocarbons, such as trichloroethylene or R-133a (2-chloro-1,1,1-tri fluoroethane) with HF. It may also be prepared by hydrogenation of R-114a (2,2-dichloro-1,1,1,2-tetrafluoroethane) or R-124 (2-chloro-1,1,1,2-tetrafluoroethane).

It is characteristic of such reactions that many by-products are formed, containing varying numbers of hydrogen, chlorine, and fluorine atoms on methane, ethane, and ethylene molecules. These by-products and the unreacted feed material may be separated by distillation where possible. Some compounds are relatively harmless since their presence does not greatly alter the physical properties for which HFC-134a is useful. A by-product which must be removed because of its toxicity is 2-chloro-1,1-difluoroethylene (R-1122), although only relatively small amounts are typically present in R-134a as formed. R-1122 has a boiling point close to that of R-134a making them difficult to separate by distillation. After distillation of the crude product, R-1122 will still be present in amounts from about 500 to 10,000 ppm (wt.). It should be reduced to below 10 ppm according to the specifications of the Panel for Advancement of Fluorocarbon Test (PAFTII). Preferably, the R-1122 should be below about 1 wt. ppm.

In U.S. Pat. No. 3,819,493 Fozzard discloses an extractive distillation process for separating 1,1-difluoroethane (R-152a) from R-134a produced by electrochemical fluorination of R-152a. The two compounds have a low relative volatility and saturated hydrocarbons having 4–10 carbon atoms are added to increase the relative volatility and facilitate their separation.

Bell in U.S. Pat. No. 4,129,603 removes R-1122 by contacting impure R-134a with an aqueous solution of a metal permanganate. The R-134a is derived from the reaction of HF with a haloethane such as 2-chloro-1,1,1-trifuluoroethane over a chromium oxide or fluoride catalyst.

A different approach to removing R-1122 from R-134a is shown by Potter in U.S. Pat. No. 4,158,675. The reaction producing R-134a takes place at temperatures in the range of 325° to 375° C. in the presence of a chromium oxide or fluoride catalyst. Potter passes the effluent of the reaction into a second reactor containing a chromium catalyst but operated at 100° to 275° C. He shows that a substantial reduction of R-1122 is obtained.

In. U.S. Pat. No. 4,906,796 one of the present inventors disclosed the removal of R-1122 from R-134a by adsorption using zeolites or carbon molecular sieves.

Further improvement in methods of purifying R-134a, particularly with respect to eliminating R-1122 is desired and the present inventors have discovered a means for purification by photochlorination which will be disclosed in detail below.

In addition, one aspect of the invention relates to a process for production of R-124 (2-chloro-1,1,1,2-tetrafluoroethane).

SUMMARY OF THE INVENTION

2-Chloro-1,1-difluoroethylene (R-1122) is removed from a mixture consisting substantially of 1,1,1,2-tetrafluoroethane (R-134a) and containing up to about 10,000 wt. ppm R-1122 by contacting the HFC-134a mixture with 1–4 mols of chlorine for each mol of R-1122 in the vapor phase in the presence of ultraviolet light having a wave length between about 300 to 400 nm which provides at least 2 watts-hour/kg of the mixture. The R1122 can be reduced to below 35 wt. ppm or lower, as it is converted to 1,1,2-trichloro-1,1-difluoroethane (R-122), which has a higher boiling point and can be easily separated from R-134a. Other unsaturated compounds are also removed by chlorination to other derivatives which can be separated.

The photochlorination of R-134a may produce as a by-product 2-chloro-1,1,1,2-tetrafluoroethane (R-124). Since this is a useful product, the loss of R-134a is not necessarily a serious problem. In fact, co-production of R-124 may be desirable. Thus, in one aspect, the invention comprises a method for reducing the R-1122 in R-134a to a low level while producing R-124 along with R-134a. Alternatively, R-124 may be produced by photochlorination of R-134a in the absence of any need to remove R-1122. In another aspect, the invention includes a process for producing R-122 from R-1122.

DETAILED DESCRIPTION OF THE INVENTION

Figure 1:
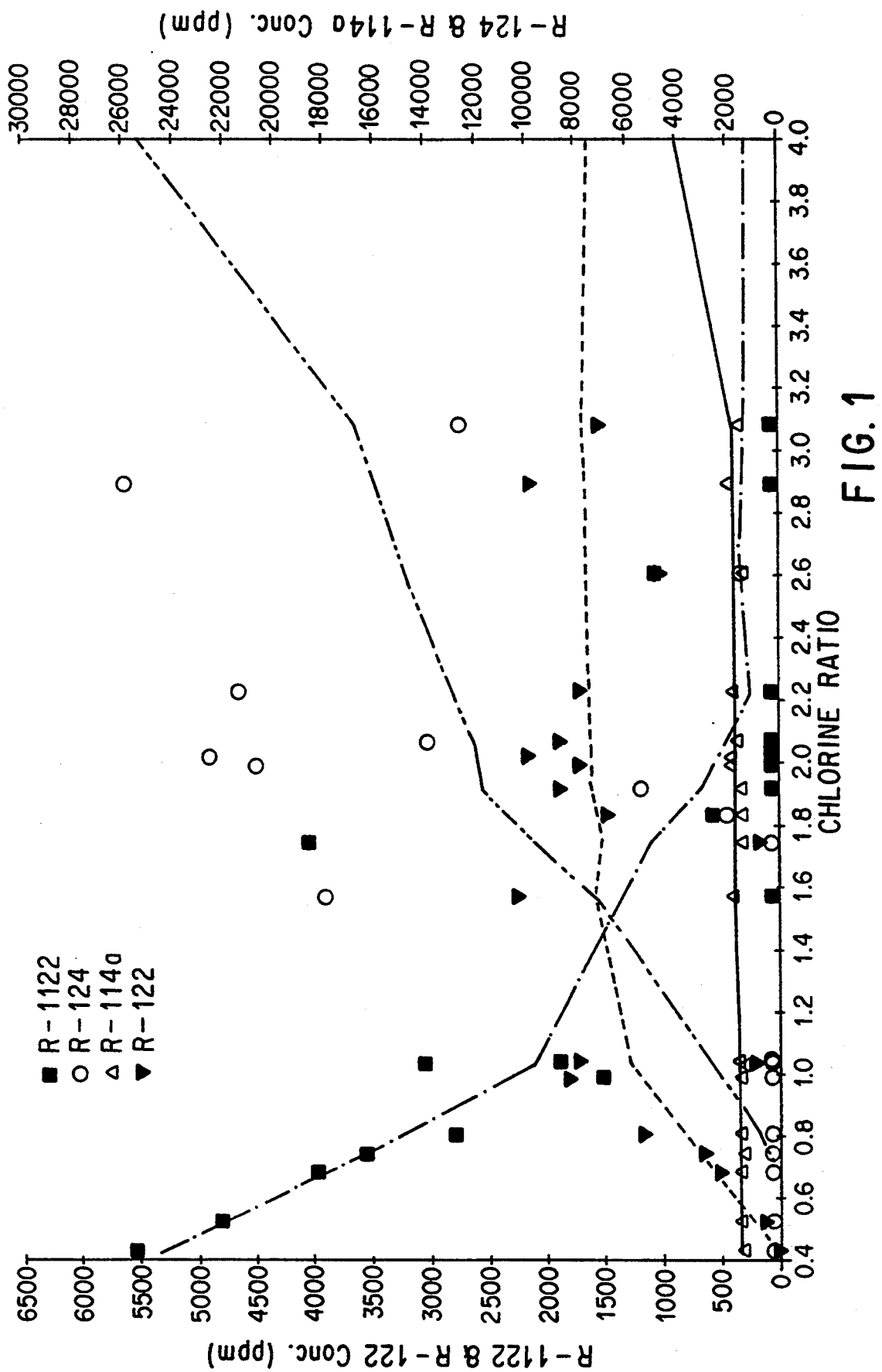
FIG. 1 is a graph showing concentration at various ratios of chlorine to R-1122.

Typically HFC-134a is produced by reacting trichloroethylene or R-133a with HF over a catalyst and will contain a variety of byproducts such as R-143a, R-1122, R-124, R-133a, R-114a. It is of particular importance to remove 2-chloro-1,1-difluoroethylene (R-1122) from the crude product. Preliminary separation of R-134a by distillation will leave about 500 to 10,000 wt. ppm of R-1122 having a boiling point of −17.1° C. compared to −26.5° C. for R-134a, the difference in boiling points making R-1122 difficult to separate from R-134a. In the process of the invention, R-1122 and other unsaturated compounds are reacted with chlorine to provide more highly chlorinated compounds which have a higher boiling point and can be readily separated from R-134a. At the same time R-124 may be co-produced by chlorination of R-134a. Alternatively, the invention includes processes for producing R-122 from R-1122 and R-124 from R-134a.

Process Conditions

In the process, crude R-134a containing about 500 to 10,000 wt. ppm of R-1122 along with minor amounts of other byproducts such as those mentioned above will be contacted with chlorine in the presence of ultraviolet light having a wavelength of about 300 to 400 nm. It should be understood that an ultraviolet lamp may have radiation outside this range also, but that photochlorination requires UV light within this range.

The ultraviolet light will have an intensity which provides an exposure greater than zero and up to about 1000 watts-hour/kg of the R-134a mixture, preferably 2 to 100 watts-hour/kg.

The ultraviolet light may be provided by arc lamps including mercury, argon, or xenon and filament lamps including tungsten and halogen.

Chlorine is introduced into the crude R-134a stream at a rate sufficient to provide about 1 to 4 mols of chlorine for each mol of R-1122.

It has been found that increasing either the ratio of chlorine to R-1122 ($Cl_2$/R-1122) or the ultraviolet light exposure improves the chlorination of R-1122. Generally, we have been able to reduce the R-1122 to below 35 wt. ppm using a UV exposure above about 5 watts-hour/kg but with very low ratios of $Cl_2$/R-1122. Conversely, much lower UV exposures can be used if higher $Cl_2$/R-1122 ratios are used. The $Cl_2$/R-1122 ratio and UV exposure may be adjusted to provide the desired set of conditions. It is believed that the actual concentration of R-1122 is much lower than 35wt. ppm. The presence of R-124a obscures the measurement of R-1122 at such low levels. Other analyses indicate that the combined amount of R-124a and R-1122 is mainly R-124a and, consequently, the actual amount of R-1122 is believed to be below 10 wt. ppm and thus should meet the desired specification.

The temperature employed may vary but may be from about −30° C. to 200° C., preferably about 0° to 80° C.

The pressure selected will be a convenient value to suit the processing conditions for R-134a and to assure that R-134a is a vapor or liquid as desired.

The UV radiation from a lamp ordinarily will be expressed as watts, which is a rate of delivering energy. For present purposes, it is considered more useful to express radiation as the quantity of energy delivered over a period of time, i.e. the "exposure," rather than as the rate. Thus, the exposure may be expressed as watts-hours, which is related to the number of photons of energy delivered and their wavelength and these, in turn, relate to the chlorination of unsaturated molecules such as R-1122. Since the exposure is the product of the rate of delivering energy (photons/time) and the time, it will be clear that either the rate or the time could be varied. However, for practical applications the rate and the time will have limits imposed by the need to carry out the desired photochlorination reaction within constraints of time and product yield. If a high rate or a long time is used, not only will R-1122 be chlorinated to R-122, but chlorine will react with other molecules, particularly with R-134a to make HCFC-124. Alternatively, if a very low rate or a short time is used, then insufficient chlorination of R-1122 would be expected.

When co-production of 2-chloro-1,1,1,2-tetrafluoroethane (R-124) is desired, the ratio of chlorine to R-134a can be increased. Preferably, the U.V. exposure will be about 2 to 160 watts-hour/kg of R-134a and the $Cl_2$/R-1122 ratio (mol) about 4 to 50. Up to about 16% of the R-134a may be converted to R-124 by this process without producing excessive amounts of R-114a. As the ratio of $Cl_2$/R-1122 is increased, the R-124 is further chlorinated in part to R-114a. If the amount of chlorine is related to the amount of R-134a rather than to the amount of R-1122, the maximum $Cl_2$/R-134a mol ratio would be about 0.24/1. It will be understood by those skilled in the art that the operating conditions may be adjusted to optimize the relative amounts of R-114a and R-134a.

After the R-134a has been photochlorinated, the chlorinated products may be separated from the HFC-134a, as, for example, by distillation, since the boiling points are no longer close to that of HFC-134a. Any residual chlorine, HCl or HF may be separated by absorption of chlorine in aqueous caustic, by adsorption on carbon molecular sieves, or reaction with aqueous sodium sulfite or sodium thiosulfate.

EXAMPLE 1

Removal of R-1122

The photochlorination of R-134a was carried out in a 125-mL pyrex pressure vessel equipped with an inlet at the bottom and an outlet at the top. The reactor vessel was placed at the focus of RPR-100 Rayonet reactor (Southern New England Ultraviolet Company) equipped with 16 RPR-3500 lamps having their peak intensity at a wavelength of 350 nm. Light below 300 nm was removed by a pyrex filter. Ferrioxalate actinometry was used to measure the radiation received (see *The Chemists Companion*, A. J. Gordon & R. A. Ford, Wiley Interscience (1972), pages 362–368). In this vessel under these conditions this procedure gave an incident light intensity of $1,448 \times 10^{-6}$ einstein/sec (0.497 watts). (One einstein is an equal to a mol of photons.)

Two feed streams were passed through separate lengths of capillary tubing and then mixed and passed into the reactor at 5 psig (34.5 kPa gauge). The impure R-134a contained 6000 wt. ppm R-1122 plus other impurities including R-134 which is converted to R-124a by photochlorination. One stream contained impure R-134a while the second contained chlorine. By blending the two streams the ratio of chlorine to R-1122 was varied. The radiation exposure was calculated from the residence time and the light intensity and varied from 5.89 to 27.5 watts-hour/kg. After exposure to the ultraviolet light the product stream was analyzed by gas chromatography using a 3048 mm long×3,175 ntm diameter column of 1% SP1000 on 60-80 mesh Carbopack B (Supelco Inc.) packing operated at 45° C. for 3 minutes and then programmed to increase 8° C./min to 200° C. As previously noted, R-124a and R-1122 are seen in this analysis as a single compound, consequently, the reported value for R-1122 is considered to be much below 35 wt. ppm and likely below 10 wt. ppm. It is to be understood that the FIG. 35 wt. ppm R-1122 represents the maximum value and in practice would be adjusted to account for R-124a.

The results of the tests at lower ratios of $Cl_2$/R-1122 are given in FIG. 1. The compounds are designated as refrigerants (R) according to the commonly used system of the American Society of Refrigerating Engineers.

It can be seen that the concentration of R-1122 decreases as the ratio of $Cl_2$/R-1122 is increased. Theoretically one mol of chlorine can react with one mol of R-1122 to yield one mol of R-122. The results show that at a ratio of about 1.6/1 essentially all of the R-1122 has been converted within the limits of analytical precision. The product of chlorination of R-134a, i.e., R-124 is seen to appear at a ratio of about 1/1. Therefore, the preferred ratio of $Cl_2$/R-1122 is considered to be about 1/1 to 1.6/1 when only the removal of R-1122 is desired.

EXAMPLE 2

Co-Production of R-124

Figure 2:
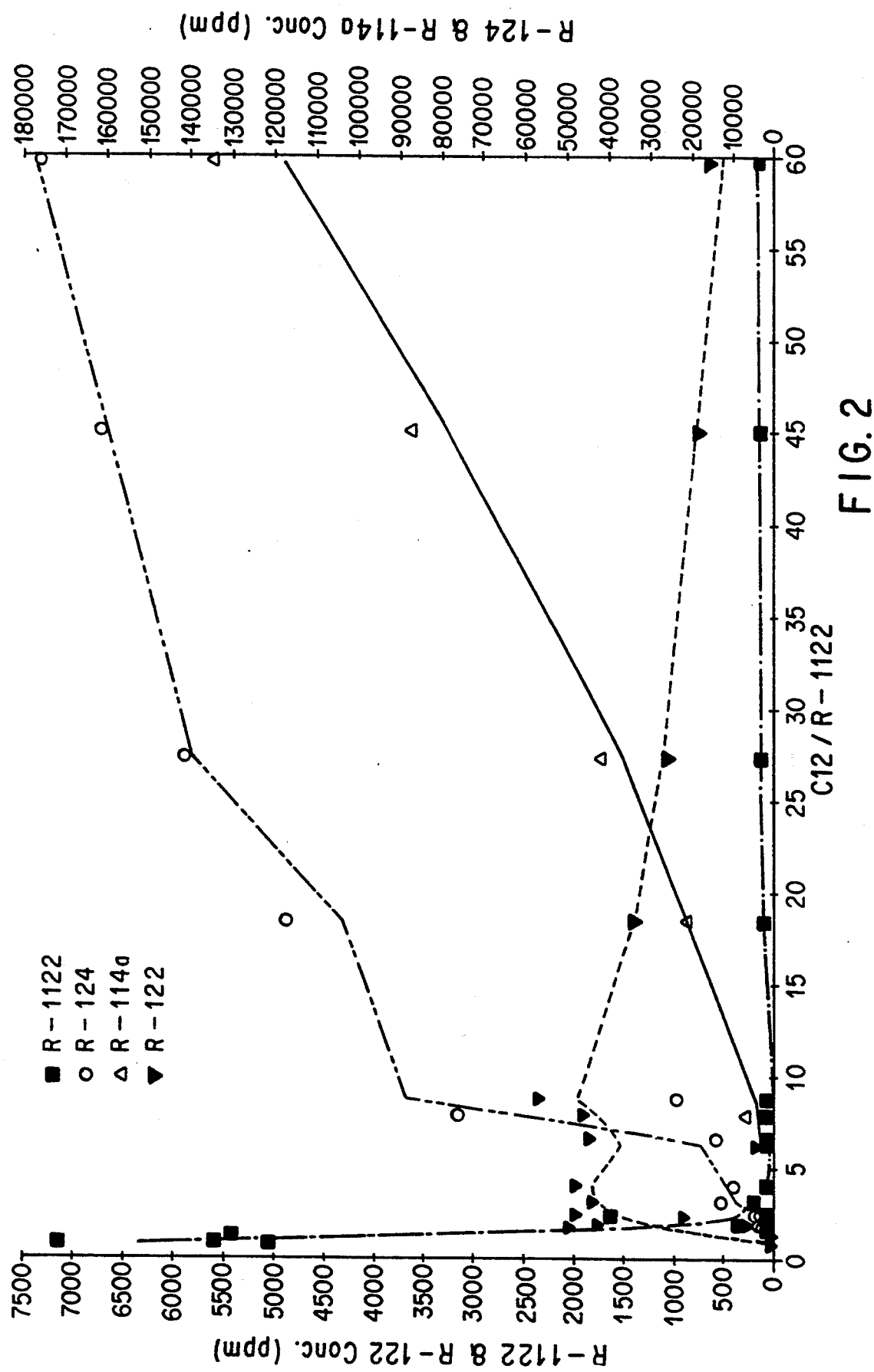
FIG. 2 is a graph similar to FIG. 1 including higher ratios of chlorine to R-1122.

The photochlorination of R-134a was carried out in the same experimental apparatus and procedures used in Example 1. Two feed streams were passed separately through capillaries to and then mixed and passed into the reactor at 5 psig (34.5 kPa gauge). One stream contained impure R-134a, while the second contained chlorine. By blending the two streams, the ratio of chlorine to R-1122 was varied. Residence time in the reactor was determined by the sum of the two flow rates, and exposure was calculated from the residence time and the light intensity. After exposure to the ultraviolet light the product stream was condensed and analyzed by gas chromatography as described in Example 1. The results of tests with ratios of $Cl_2$/R-1122 higher than those of Example 1 are shown in FIG. 2. At the left of the graph the results of the previous example are seen, that is, R-1122 is removed to near the zero level. As the $Cl_2$/R-1122 ratio is increased chlorination of R-134a to R-124 and R-124 to R-114a is increased. At the extreme right end of the graph it can be seen that the amount of R-124 is above 15 mol % and R-114a above 10 mol %. Therefore, by adjusting the amount of chlorine present it is possible to produce significant quantities of R-124. Producing R-114a is less desirable and the optimum ratio of $Cl_2$/R-1122 is considered to be about 5/1 to 21/1.

Although the process of the invention has been described as one in which R-1122 is considered an impurity in R-134a and removed to the desired low level, the invention may also be considered to include the co-production of R-124 from R-134a and more generally, processes in which R-134a is converted to R-124 or R-1122 is converted to R-122.

We claim:

1. A process for removing 2-chloro-1,1-difluoroethylene (R-1122) and unsaturated by-product compounds from 1,1,2,-tetrafluoroethane (R-134a) comprising
   (a) contacting a mixture consisting essentially of R-134a and up to about 10,000 wt. ppm R-1122 with about 1-4 mols of chlorine for each mol of R-1122 in the presence of ultraviolet light having wavelengths between about 300 and 400 nm providing an exposure greater than zero and up to about 1000 watts-hour/kg of said mixture, thereby reducing the concentration of R-1122 to less than 35 wt. ppm by converting said R-1122 to 1,2,2-trichloro-1,-difluoroethane (R-122); and
   (b) separating the R-122 formed in (a) from R-134a.

2. The process of claim 1 wherein said R-134a is chlorinated in part to co-produce 2-chloro-1,1,1,2-tetrafluoroethane (R-124).

3. The process of claim 1 wherein said ultraviolet light provides an exposure of about 2 to 100 watts-hour/kg of said mixture.

4. The process of claim 1 wherein the contacting of (a) is carried out at a temperature of about −30° to 200° C.

5. The process of claim 1 wherein the separation of (b) is carried out by distillation.

6. A process for producing 2-chloro-1,1,2,-tetrafluoroethane (R-124) from 1,1,1,2-tetrafluoroethane (R-134a) comprising
   (a) contacting a mixture consisting essentially of R-134a with greater than zero up to about 0.24 mols of chlorine for each mol of said R-134a to produce a desired amount of R-124 in the presence of ultraviolet light having wavelengths between about 300 and 400 nm providing an exposure greater than zero and up to about 1000 watts-hour/kg of said R-134a to produce R-124 by photochlorination;
   (b) separating the R-124 produced in (a) from R-134a.

7. The process of claim 6 wherein R-124 is up to 16% based on the R-134a feed to the chlorination of step (a).

8. A process for producing 1,2,2-trichloro-1,1-difluoroethane (R-122) from 2-chloro-1,1-difluoroethylene (R-1122comprising
   (a) contacting a mixture consisting essentially of R-1122 with about 1-4 mols of chlorine for each mol of R-1122 in the presence of ultraviolet light having wavelengths between about 300 and 400 nm providing an exposure greater than zero and up to about 1000 watts-hour/kg of said R-1122, thereby producing R-122;
   (b) separating the R-122 formed in (a) from R-1122.

* * * * *

UNITED STATES PATENT AND TRADEMARK OFFICE
CERTIFICATE OF CORRECTION

PATENT NO. : 5,336,377
DATED : August 9, 1994
INVENTOR(S) : Yates et al.

It is certified that error appears in the above-identified patent and that said Letters Patent is hereby corrected as shown below:

Column 2, line 14: "R1122" should read --R-1122--
Column 2, line 15: 1,1,2-trichloro-1,1-difluoroethane"..should read
   --1,2,2-trichloro-1,1-difluoroethane"--
Column 4, line 42: "3,175 ntm" should read --3.175 mm--
Column 5, line 39: "1,1,1,2,-" should read --1,1,1,2- --
Column 6, line 35: "(R-1122comprising" should read --(R-1122) comprising Signed and Sealed this Tenth Day of January, 1995

Attest:

BRUCE LEHMAN

Attesting Officer    Commissioner of Patents and Trademarks